United States Patent
Gutek et al.

[11] Patent Number: 6,133,370
[45] Date of Patent: Oct. 17, 2000

[54] SILICONE POLYETHERS WITH ARYLALKYL GROUPS

[75] Inventors: Beth Irene Gutek, Freeland; Alan Zombeck, Midland, both of Mich.

[73] Assignee: Dow Corning Corporation, Midland, Mich.

[21] Appl. No.: 09/253,926

[22] Filed: Feb. 22, 1999

[51] Int. Cl.[7] .................. C08K 3/12; C08J 3/07
[52] U.S. Cl. .............. 524/588; 556/445; 528/29; 528/31; 528/43; 424/401; 514/941; 252/308; 252/312
[58] Field of Search .................. 556/445; 252/308, 252/312; 424/401; 514/941; 524/588; 528/29, 31, 43

[56] References Cited

U.S. PATENT DOCUMENTS

| | | | |
|---|---|---|---|
| 3,657,305 | 4/1972 | Morehouse | 260/448.2 B |
| 3,686,254 | 8/1972 | Morehouse | 528/31 |
| 5,227,200 | 7/1993 | Legrow | 427/387 |
| 5,384,383 | 1/1995 | Legrow | 528/23 |
| 5,389,365 | 2/1995 | Legrow | 424/78 |
| 5,578,692 | 11/1996 | Biggs | 528/15 |

*Primary Examiner*—Margaret G. Moore
*Attorney, Agent, or Firm*—James L. DeCesare

[57] ABSTRACT

A composition which is a silicone polyether containing arylalkyl groups, most preferably an arylalkyl group such as the 2-phenylpropyl group, i.e., $-CH_2CH(C_6H_5)CH_3$. The compositions demonstrate improvements in emulsification over silicone polyethers without such arylalkyl groups. The compositions have a formula generally corresponding to $$R_3SiO(R_2SiO)_x(RQSiO)_y(RQ'SiO)_zSiR_3$$

in which R is an alkyl group, Q is a polyoxyalkylene block, Q' is an arylalkyl radical, x is 0–500, y is 1–50, and z is 1–50. The compositions and emulsions containing the compositions have general utility, but are especially useful in the personal care arena.

5 Claims, No Drawings

SILICONE POLYETHERS WITH ARYLALKYL GROUPS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to silicone polyethers with arylalkyl groups preferably 2-phenylpropyl arylalkyl groups, i.e., —$CH_2CH(C_6H_5)CH_3$. These new silicone polyethers show improved emulsification over silicone polyethers without arylalkyl groups such as 2-phenylpropyl groups. Thus, (i) they are capable of forming water-in-organic oil or water-in-silicone oil emulsions at lower use levels; (ii) they exhibit higher emulsion stability in silicone and ester blended oil phases; and (iii) they produce stable emulsions in low viscosity, low internal phase formulations.

BACKGROUND OF THE INVENTION

While U.S. Pat. No. 5,227,200 (Jul. 13, 1993), and U.S. Pat. No. 5,384,383 (Jan. 24, 1995), both of which are assigned to the same assignee as the present invention, describe silicone polymers containing 2-phenylpropyl groups, none of the silicone polymers in the '200 patent or the '383 patent are silicone polyethers, nor are they terpolymeric types of silicone polyethers.

A third U.S. Pat. No. 5,389,365 (Feb. 14, 1995), also assigned to the same assignee as the present invention, describes silicone terpolymers containing polyether substitution, but the '365 patent does not include silicone terpolymers containing arylalkyl groups such as 2-phenylpropyl groups.

In contrast, the present invention relates to novel arylalkyl functional silicone polyethers, their preparation, and stable water-in-silicone oil emulsions prepared with the arylalkyl functional silicone polyethers. Such compositions were found to exhibit improved performance over standard commercially available silicone polyethers which did not contain arylalkyl groups such as 2-phenylpropyl groups. In addition, they exhibit better performance in low internal phase emulsions, better tolerance to certain esters, and are effective at lower active levels.

BRIEF SUMMARY OF THE INVENTION

This invention is directed to silicone polyethers generally corresponding to the formula

in which R is an alkyl group, Q is a polyoxyalkylene block containing a linking group and a terminating group, Q' represents an arylalkyl radical, x is 0–500, y is 1–50, and z is 1–50.

The invention is also directed to emulsions containing these novel types of silicone polyethers.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Silicone polyethers according to the present invention generally correspond to, and can be generally described with reference to the formula:

In the formula, R represents in alkyl group containing 1–6 carbon atoms such as methyl, ethyl, propyl, and butyl. R is most preferably methyl.

Q represents a polyoxyalkylene block containing a linking group and a terminating group. The polyoxyalkylene block can be represented by the formula

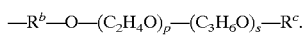

The linking group $R^b$ is —$C_mH_{2m}$—. The terminating group $R^c$ is hydrogen or an alkyl group of one to six carbon atoms. m in the linking group has a value of two to eight. p and s in the oxyalkylene segment of the block each have a value such that the oxyalkylene segment —$(C_2H_4O)_p$—$(C_3H_6O)_s$— of the polyoxyalkylene block has a molecular weight in the range of about 300 to about 5,000.

The oxyalkylene segment preferably has 50–99 mole percent of oxyethylene units —$(C_2H_4O)_p$— and 1–50 mole percent of oxypropylene units —$(C_3H_6O)_s$—.

The terminating group $R^c$ is preferably a methyl group. m is preferably three or four. p and s preferably each have a value to provide a molecular weight for oxyalkylene segment —$(C_2H_4O)_p$—$(C_3H_6O)_s$— of between about 400 to about 3,000. Most preferably, p and s each have values of about 1 to about 28. If desired, however, s can also be equal to zero.

Q' represents an arylalkyl racical selected from the group consisting of phenylmethyl(benzyl), 1-phenylethyl, 2-phenylethyl, 2-phenylpropyl, 1-plenylbutyl, 4-phenylbutyl, and 2-phenylheptyl. Preferably, Q' is 2-phenylpropyl.

x has a value of 0–500, preferably 1–400, and most preferably 50–200. y has a value of 1–50, preferably 1–25, and most preferably 1–10. z has a value of 1–50, preferably 1–25, and most preferably 1–10.

The structure of these silicone polyethers can be varied and modified, such as to provide silicone polyether polymers, copolymers, and terpolymers containing:

1. A weight percent of ethylene oxide in the polymer ranging from about 5 to about 20 percent;
2. A weight percent of arylalkyl, e.g., 2-phenylpropyl, in the polymer ranging from about 1 to about 15 percent; and
3. A degree of polymerization DP, i.e., x+y+z, of about 70 to about 500, preferably about 100 to about 400.

The methods which can be used to prepare these silicone polyethers are generally known in the art. Thus, one of the methods can involve the hydrosilylation of an ≡SiH containing siloxane with an alkenylbenzene, in the presence of a platinum catalyst such as chloroplatinic acid, as described in the '200 patent.

Another method is described in the '365 patent and can involve combining stoichiometric amounts of an ≡SiH containing siloxane with an alkenyl ether terminated organic oxyalkylene compound, in the presence of a platinum catalyst such as chloroplatinic acid. In methods according to the present invention, it is preferred to employ an alkenyl ether terminated organic oxyalkylene compounds which contains at least three to about ten carbon atoms in the alkenyl group, examples of which are allyl, isopropenyl, 2-butenyl, 3-butenyl, or hexenyl. Allyl is the most preferred alkenyl group, however.

Some representative allyl ether terminated organic oxyalkylene compounds include $H_2C=CH-CH_2-O-(CH_2-CH_2O)_a-R'$; $H_2C=CH-CH_2-O-[CH_2-CH(CH_3)O]_b-R'$; and $H_2C=CH-CH_2-O-(CH_2-CH_2O)_a-[CH_2-CH(CH_3)O]_b-R'$; in which a is 1–120; b is 1–50; and R' is hydrogen or an alkyl radical containing 1–6 carbon atoms, such as methyl, ethyl, propyl, or butyl. In the examples set forth below, the allyl ether terminated organic oxyalkylene compound used was a polyethylene oxide monoallylether containing 7 moles of ethylene oxide.

A third method can involve the preparation of a trimethylsiloxy-endcapped methylhydrogen siloxane, via an anhydrous triflic acid, i.e., trifluoromethane sulfonic acid, catalyzed polymerization of hexamethyldisiloxane, tetramethylcyclotetrasiloxane, and pentamethylcyclopentasiloxane. Such a method is described in detail, for example, in U.S. Pat. No. 5,578,692 (Nov. 26, 1996), which is another patent assigned to the same assignee as the present invention.

These and other similar methods for preparing silicone polyethers are also described in detail in the standard text on silicone chemistry, entitled *Chemistry and Technology of Silicones,* by Walter Noll, Academic Press, Inc., New York, N.Y., Pages 373–376, (1968).

The general procedure for preparing emulsions according to the present invention is described in detail in Example 4.

EXAMPLES

The following examples are set forth in order to illustrate this invention in more detail.

Example 1

Step 1—Preparation of $Me_3SiO-(Me_2SiO)_x-(MeHSiO)_y-(MeQ'SiO)_z-SiMe_3$ by Acid Equilibration Where Q' is 2-phenylpropyl, x is 69, y is 1.6, z is 1.9, and Me is Methyl

| Ingredients | Weight % | Gram |
| --- | --- | --- |
| Hexamethyldisiloxane | 2.84 | 7.1 |
| Dimethylcyclosiloxane | 98.57 | 223.9 |
| Methylhydrogen cyclosiloxane | 1.68 | 4.2 |
| 2-phenylpropylmethyl cyclosiloxane | 5.91 | 17.75 |
| Trifluoromethane sulfonic acid | 0.09 | 0.3 |

In a three-necked round bottom flask equipped with stirrer, reflux condenser, thermometer and nitrogen blanket, mix all of the above ingredients. Heat to 65° C. and hold at 65–70° C. for 5 hours. Cool to 60° C., add 3 g sodium bicarbonate and 3 g diatomaceous earth, and stir for 1 hours to neutralize. Filter through a 0.45 micron membrane filter.

Step 2—Addition of Polyether Functionality

| Ingredients | Weight % | Gram |
| --- | --- | --- |
| Polyethylene oxide monoallyl ether, 7 mole ethylene oxide | 11.9 | 23.8 |
| Siloxane prepared above | 88.1 | 176.2 |
| 2-propanol | 25 pph* | 50 |
| Potassium acetate | 250 ppm | 0.05 |
| Chloroplatinic acid | 10 ppm Pt | |

*=parts per hundred

In a three-necked round bottom flask equipped with stirrer, reflux condenser, thermometer and nitrogen blanket, mix all of the above ingredients except chloroplatinic acid. Heat to 80° C. and add chloroplatinic acid. Continue heating to reflux and hold until $\equiv$SiH is consumed. Remove 2-propanol by vacuum distillation.

Example 2

Direct Hydrosilylation Followed by Acid Equilibration and Addition of Polyether Functionality Step 1

| Ingredients | Weight % | Gram |
| --- | --- | --- |
| $Me_3SiO-(Me_2SiO)_{8.7}-(MeHSiO)_{3.7}-SiMe_3$ | 51.6 | 107 |
| α-methylstyrene, $C_6H_5C(CH_3)=CH_2$ | 12.08 | 25 |
| Chloroplatinic acid | 10 ppm Pt | |

In a three-necked round bottom flask equipped with stirrer, reflux condenser, thermometer and nitrogen blanket, add the siloxane component. Heat to 50° C. and add chloroplatinic acid. Heat to 70° C. and add α-methylstyrene drop-wise over a 45 min period. Heat to 120° C. and hold until alpha-methylstyrene is consumed. Cool to room temperature.

Step 2—Dimethyl "D" unit $(CH_3)_2SiO=$ Increase by Acid Equilibration

| Ingredients | Weight % | Gram |
| --- | --- | --- |
| Hexamethyldisiloxane | 79.3 | 198.3 |
| Siloxane made in Step 1 | 20.7 | 51.75 |
| Trifluoromethane sulfonic acid | 0.09 | 0.3 |

In a three-necked round bottom flask equipped with stirrer, reflux condenser, thermometer and nitrogen blanket, mix all of the above ingredients. Heat to 65° C. and hold at 65–70° C. for 5 hours. Cool to 60° C., add 3 g sodium bicarbonate and 3 g diatomaceous earth, and stir for 16 hours to neutralize. Filter through a 0.45 micron membrane filter.

Step 3—Addition of Polyether Functionality

| Ingredients | Weight % | Gram |
| --- | --- | --- |
| Polyethylene oxide monoallylether 7 moles ethylene oxide | 11.9 | 23.8 |

-continued

| Ingredients | Weight % | Gram |
| --- | --- | --- |
| Siloxane prepared above | 88.1 | 176.2 |
| 2-propanol | 25 pph | 50 |
| Potassium acetate | 250 ppm | 0.05 |
| Chloroplatinic acid | 10 ppm Pt | |

In a three-necked round bottom flask equipped with stirrer, reflux condenser, thermometer and nitrogen blanket, mix all of the above ingredients except chloroplatinic acid. Heat to 80° C. and add chloroplatinic acid. Continue heating to reflux and hold until ≡SiH is consumed. Remove 2-propanol by vacuum distillation.

Example 3

Step 1—Acid Equilibration of an ethylmethyl/methyl 2-phenylpropyl/siloxane Polymer

| Ingredients | A | B | C | D | E | F |
| --- | --- | --- | --- | --- | --- | --- |
| Ethylmethyl/methyl 2-phenylpropyl sioloxane polymer | 132.14 | 132.33 | 171.18 | 93.43 | 44.48 | 93.43 |
| Hexamethyldisiloxane | 0.92 | 4.31 | 1.23 | 2.81 | 2.61 | 2.81 |
| Dimethylcyclosiloxane | 456.63 | 453.09 | 411.32 | 487.43 | 542.55 | 487.43 |
| Methylhydrogen cyclosiloxane | 10.31 | 10.27 | 16.27 | 16.33 | 10.36 | 16.33 |
| Total - Gram | 600.0 | 600.0 | 600.0 | 600.0 | 600.0 | 600.0 |

In a three-necked round bottom flask equipped with stirrer, reflux condenser, thermometer and nitrogen blanket, mix all of the above ingredients, and add 0.6 ml trifluoromethane sulfonic acid. Heat to 65° C. and hold at 65–70° C. for 5 hours. Cool to 60° C., add 3 g sodium bicarbonate and 3 g diatomaceous earth, and stir for 16 hours to neutralize. Filter through a 0.45 micron membrane filter.

Step 2—Addition of Polyether Functionality

Repeat Step 2 in Example 1, or Step 3 in Example 2.

The compatibility in a variety of formulating materials, of a siloxane prepared according to the procedure outlined in Example 1 Step 1 without polyether functionality, was compared to that of a polydimethylsiloxane (PDMS) having about an equivalent molecular weight. In at least two instances, an enhanced solubility was found at a 50/50 ratio, namely with an 8 centistoke (mm$^2$/s) mineral oil and neopentyl glycol dicaprylate/dicaprate. This data is shown in Table 1.

TABLE 1

Oil Compatibility of 2-Phenylpropyl Siloxane
Ratio = Weight of Silicone/Weight of Oil

| | 90/10 ratio | | 50/50 ratio | | 10/90 ratio | |
| --- | --- | --- | --- | --- | --- | --- |
| OILS | Dimethyl Siloxane | 2-Phenyl propyl Siloxane | Dimethyl Siloxane | 2-Phenyl propyl Siloxane | Dimethyl Siloxane | 2-Phenyl propyl Siloxane |
| Finsolv TN | C | C | IC | IC | IC | IC |
| Coconut Oil | cloudy | cloudy | IC | IC | cloudy | cloudy |
| Corn Oil | IC | IC | IC | IC | IC | IC |
| Ethanol | IC | IC | IC | IC | IC | IC |
| Jojoba Oil | IC | IC | IC | IC | IC | IC |
| Mineral Oil 8 mm$^2$/s | C | C | IC | C | IC | IC |
| Sunflower Oil | IC | IC | IC | IC | IC | IC |
| Isopropyl palmitate | C | C | C | C | C | C |
| Isopropyl myristate | C | C | C | C | C | C |
| Tridecyl Neo pentanoate | C | C | C | C | C | C |
| Neopentyl Glycol Dicaprylate Dicaprate | C | C | IC | C | IC | IC |

In Table 1, "C" indicates that the combination of ingredients is compatible and that the combination results in a clear mixture. "IC" indicates that the combination of ingredients is incompatible, and that the combination forms two phases. "Cloudy" means that the combination of ingredients is stable, but that the mixture is cloudy. The oil identified as FINSOLV TN in Table 1 is a tradename of Finetex Incorporated, Elmwood Park, New Jersey, for a liquid $C_{12}$ to $C_{15}$ allyl benzoate. The oil tridecyl neopentanoate is the ester of tridecyl alcohol and neopentanoic acid. The oil neopentyl glycol dicaprylate/dicaprate is the diester of neopentyl glycol and a blend of caprylic acid and capric acid.

Example 4

Performance in Emulsion Formulations 1 & 2

In order to further demonstrate the benefits of the silicone polyether emulsifiers of the present invention, representative emulsifiers were dispersed in a cyclic dimethylsiloxane at variable concentrations to facilitate their handling. The emulsion formulations were prepared based upon the amount of active emulsifier, i.e., the weight percent of the emulsifier in the dispersion. Thus, the "active emulsifier" shown in Table 2 is the amount of the dispersion x the percent of its non-volatile content (NVC). The balance of the oil phase in the emulsions was comprised of the cyclic dimethylsiloxane ingredient, which in this case, was decamethylcyclopentasiloxane, shown in Table 2 as $D_5$. The "Silicone Blend" used in Table 2 was an ultra-high viscosity linear polydimethylsiloxane gum dispersed in the volatile cyclomethicone $D_5$ fluid.

TABLE 2

|  | Emulsion Formulation 1 | | Emulsion Formulation 2 | |
| --- | --- | --- | --- | --- |
| Oil phase | Weight % | Gram | Weight % | Gram |
| $D_5$ | balance | balance | balance | balance |
| Silicone Blend | 10.0 | 24.0 | 0 | 0 |
| Active Emulsifier | 1.05 | 2.52 | 1.05 | 2.52 |
| Total | 25.0 | 60.0 | 30.0 | 72.0 |
| Water Phase | Weight % | Gram | Weight % | Gram |
| Water | 73.5 | 176.4 | 68.5 | 164.4 |
| Tween 20 | 0.5 | 1.2 | 0.5 | 1.2 |
| NaCl | 1.0 | 2.4 | 1.0 | 2.4 |
| Total | 75.0 | 180.0 | 70.0 | 168.0 |

It should be noted that the Emulsion Formulation 1 shown in Table 2 is a high-viscosity or "cream-type", high internal phase emulsion; whereas the Emulsion Formulation 2 is a low-viscosity or "lotion-type" emulsion.

These emulsions were prepared in 400 and 600 ml beakers using a high speed rotary mixer having a single shaft with double blades set one inch apart, a lower blade that was two inches in diameter, and a top blade that was 2½ inches in diameter. The procedure involved weighing components of the water phase in a 400 ml beaker and mixing them until it was homogenous and smooth, avoiding air entrapment. The next step was to weigh the components of the oil phase in a 600 ml beaker and mix them until homogenous and smooth, again avoiding air entrapment. With the mixer in the 600 ml beaker containing the oil phase, it was set so that the bottom of blade was just clear of the bottom of the beaker. The speed of the mixer was gradually increased to 1376 RPM. The final step was to add the water phase over a 15–20 minute period, and continue mixing the emulsion for an additional period of 15 minutes.

The viscosity was measured with a Brookfield rotational viscometer with a heliopath stand, and is indicative of the emulsion particle size. Thus, within a given Emulsion Formulation, the higher the viscosity, the lower is the particle size, and the more narrow is the particle size distribution. In general, a high comparative viscosity indicates stability.

Oven stability was determined and represents accelerated aging and storage of Emulsion Formulations in hot climates. Freeze/thaw cycles were also measured, and the cycles were conducted at temperatures of −20° C. to +22° C. These cycles represent the shipping and storage characteristics of Emulsion Formulations in cold climates. The results can be expressed as the number of cycles before the Emulsion Formulation shows signs of separation. The maximum number of cycles is generally considered to be 5 cycles.

The results of these evaluations are shown in Table 3. For purposes of comparison, a standard commercial grade silicone polyether was employed. It is referred to hereinafter as well as in the accompanying Tables as Comparative SPE. Such commercial grade silicone polyethers are available from the Dow Corning Corporation, Midland, Mich. U.S.A.

The Comparative SPE was a species of a genus of siloxane polyethers of approximate structure:

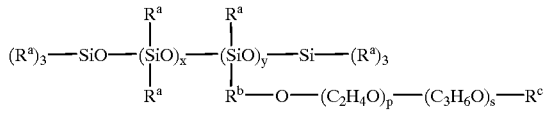

where $R^a$ is generally an alkyl group of one to six carbon atoms; $R^b$ is —$C_mH_{2m}$—; $R^c$ is hydrogen, an alkyl group of one to six carbon atoms; m has a value of two to eight; p and s have values such that oxyalkylene segment —$(C_2H_4O)_p$—$(C_3H_6O)_s$— has a molecular weight in the range of 300 to 5,000; the segment preferably having 50–99 mole percent oxyethylene units —$(C_2H_4O)_p$— and 1–50 mole percent oxypropylene units —$(C_3H_6O)_s$—; x has a value of 80–400; and y has a value of 2–10.

In most commercial grade silicone polyethers, $R^a$ and $R^c$ are methyl groups; m is three or four; and the values of p and s are such as to provide a molecular weight of the oxyalkylene segment —$(C_2H_4O)_p$—$(C_3H_6O)_s$— of between 400 to 3,000. Typically, p and s each have a value of about 18 to 28.

Silicone polyethers of this type are generally known in the art, and are described in numerous patents including, for example, U.S. Pat. No. 4,122,029 (Oct. 24, 1978), U.S. Pat. No. 4,268,499 (May 19, 1981), U.S. Pat. No. 4,311,695 (Jan. 19, 1982), U.S. Pat. No. 4,268,499 (May 19, 1981), U.S. Pat. No. 5,302,382 (Apr. 12, 1994), and U.S. Pat. No. 5,443,760 (Aug. 22, 1995), all of which are assigned to the same assignee as the present invention.

Silicone polyethers of this tape have done well in the market place, and perform particularly well in high viscosity, high internal phase emulsions such as clear gel antiperspirants. Such materials are versatile, yet possess some shortcomings in specific areas. For example, in low viscosity formulations that are not thickened and have a low internal phase content, emulsions containing such materials tend to cream downward, forming a silicone layer at the top, i.e., a phenomenon know as syneresis. In addition, it is difficult to formulate a significant amount of ester-type ingredients into emulsions with such materials. Furthermore, in many instances, there is a need to formulate products using lower levels of the active emulsifier than is currently allowed with silicone polyethers of such type.

The following results illustrate improvements in many of these areas which can be obtained with silicone polyethers according to this invention in contrast to the Comparative SPE types of materials.

As can be seen in Table 3, in Emulsion Formulation 1, all of the emulsifiers performed equivalently, and their performances could be evaluated on a scale as being about fair. In Emulsion Formulation 2, the Comparative SPE fell short of perfect stability, whereas some of the 2-phenylpropyl functional silicone polyether emulsifiers of the present invention performed somewhat better, most notably SPE F.

TABLE 3

| | Emulsion Formulation 1 | | | | Emulsion Formulation 2 | | | |
|---|---|---|---|---|---|---|---|---|
| SPE | Initial viscosity mm²/s | Oven stable 40° C., months 3 max | Oven stable 50° C., one month p/f | Freeze thaw cycle | Initial visc, mm²/s | Oven stable 40° C., months 3 max | Oven stable 50° C., 1 month p/f | Freeze thaw p/f |
| | (Me2) (2-phenylpropyl methyl) (polyether methyl) Terpolymer | | | | | | | |
| A | 161,000 | >1 | P | 5 | 5,000 | f | f | 5 |
| B | 137,000 | >1 | P | 5 | 6,000 | | top | 5 |
| C | 108,000 | >1 | P | 5 | 2,100 | f | f | 5 |
| D | 135,000 | >1 | P | 5 | 2,900 | | top | 5 |
| E | 142,000 | >1 | P | 5 | 5,000 | f | f | 5 |
| F | 270,000 | >1 | P | 5 | 3,100 | | P | 5 |
| | | | | Comparative | | | | |
| SPE | 125,000 | 3 | P | 5 | 3,600 | top | top | 4 |

In Table 3, P means that the Emulsion Formulation passed without separation of any type. f means that it failed and indicates the formation of a water layer which is indicative of coalescence of the internal phase. top means that an oil layer was formed indicative of flocculation of the emulsion particles but without coalescence of the internal phase.

Example 5

The amount of active emulsifier in the Emulsion Formulation 1 of Table 2 was varied, and the balance of the Emulsion Formulation was adjusted using volatile cyclomethicone fluid $D_5$ in order to maintain a constant phase ratio. Otherwise, the procedure carried out in Example 4 was repeated, and the results are shown in Table 4.

As can be seen in Table 4, of the three emulsifiers of the present invention which were tested, two performed at least equal to or better than the Comparative SPE ("Compar. SPE"). It should be noted that emulsifier D performed perfectly.

TABLE 4

Emulsifiers at Lower Active Levels in Formulation 1

| Composition | A | D | E | Compar. SPE |
|---|---|---|---|---|
| 1.58 Percent Active | | | | |
| Initial viscosity, mm²/s | 102,000 | 124,000 | 119,000 | 202,000 |
| Oven stability, 40° C. months (3 max) | >1 | >1 | >1 | >1 |
| Oven stability, 50° C. 1 month, P/F | P | P | P | P |
| Freeze/thaw cycle | 5 | 5 | 5 | 5 |
| 1.05 Percent Active | | | | |
| Initial viscosity, mm²/s | 161,000 | 135,000 | 142,000 | 138,000 |
| Oven stability, 40° C. months (3 max) | >1 | >1 | >1 | 3 |
| Oven stability, 50° C. 1 month, P/F | P | P | P | P |
| Freeze/thaw 0.8 Percent Active | 5 | 5 | 5 | 5 |
| Initial viscosity, mm²/s | 71,000 | 122,000 | 113,000 | 127,000 |
| Oven stability, 40° C. months (3 max) | >1 | >1 | >1 | >1 |
| Oven stability, 50° C. 1 month, P/F | P | P | P | P |

TABLE 4-continued

Emulsifiers at Lower Active Levels in Formulation 1

| Composition | A | D | E | Compar. SPE |
|---|---|---|---|---|
| Freeze/thaw cycle | 4 | 5 | 5 | 5 |
| 0.55 Percent Active | | | | |
| Initial viscosity, mm²/s | 56,000 | 116,000 | 90,000 | 90,000 |
| Oven stability, 40° C. months (3 max) | >1 | >1 | >1 | >1 |
| Oven stability, 50° C. 1 month, P/F | P | P | P | P |
| Freeze/thaw cycle | 2 | 5 | 5 | 2 |
| 0.3 Percent Active | | | | |
| Initial viscosity, mm²/s | fail | 75,000 | 58,000 | 74,000 |
| Oven stability, 40° C. months (3 max) | — | >1 | >1 | >1 |
| Oven stability, 50° C. 1 month, P/F | — | P | P | P |
| Freeze/thaw cycle | — | 5 | 3 | 2 |

In Table 4, P means that the Emulsion Formulation passed without separation of any type. fail means that it failed and indicates the formation of a water layer which is indicative of coalescence of the internal phase.

Example 6

It is well know that emulsification becomes difficult when an oil phase of the emulsion contains a blend of a silicone oil and another organic oily material. One particularly difficult organic oil to emulsify in combination with a silicone oil is the FINSOLV TN ester noted above in Table 1. The purpose of this example is to highlight more benefits of the silicone polyethers of the present invention.

Thus, several emulsions were prepared containing a blend of the volatile cyclomethicone $D_5$ fluid and the FINSOLV TN $C_{12}$ to $C_{15}$ alkyl benzoate. The Emulsion Formulations are shown in Table 5 and represent blends of the FINSOLV TN ester and $D_5$ fluid at ratios of 42:50 and 50:50 Finsolv TN:$D_5$ fluid, respectively. The phase ratio and the emulsifier level were maintained constant, and the procedure for preparing these Emulsion Formulations was the same as the procedure used in Example 4.

TABLE 5

Formulations Containing Finsolv TN:D$_5$ Blends

| | Emulsion 3 | | Emulsion 4 | |
|---|---|---|---|---|
| | Weight % | Gram | Weight % | Gram |
| Oil phase | | | | |
| D5 | 13.2 | 40.02 | 11.4 | 34.50 |
| Finsolv TN | 9.6 | 28.98 | 11.4 | 34.50 |
| Active Emulsifier | 1.0 | 3.00 | 1.0 | 3.00 |
| Total | 23.8 | 72.00 | 23.8 | 72.00 |
| Water Phase | | | | |
| Water | 74.2 | 225.00 | 74.2 | 225.00 |
| Tween 20 | 1.0 | 3.00 | 1.0 | 3.00 |
| NaCl | 1.0 | 3.00 | 1.0 | 3.00 |
| Total | 76.2 | 231.00 | 76.2 | 231.00 |

As can be seen in Table 6, the Comparative SPE performed well when Finsolv TN content of the oil phase was 42 percent or less. However, at 50 percent, the Comparative SPE did not form an emulsion. Thus, it follows that any emulsifier capable of emulsification at 50 percent would be considered better.

The Emulsion Formulation C according to the present invention performed perfectly at 50 percent, and the Emulsion Formulation A according to the present invention performed nearly perfectly, as shown in Table 6.

TABLE 6

2-Phenylpropyl Emulsifiers in Finsolv TN:D5 Blend

| | 42 Percent Finsolv TN:D5 Blend | | | | 50 Percent Finsolv TN:D5 Blend | | | |
|---|---|---|---|---|---|---|---|---|
| SPE | Initial viscosity (mm$^2$/s) | Oven stable 40° C., months (3 max) | Oven stable 50° C., 1 month (p/f) | Freeze thaw cycle | Initial visc. (mm$^2$/s) | Oven stable 40° C., months (3 max) | Oven stable 50° c., 1 month (p/f) | Freeze thaw cycle |
| | | | (Me2) (2-phenylpropyl methyl) (polyether methyl) Terpolymer | | | | | |
| A | 24,000 | >1 | P | 5 | 20,000 | >1 | P | 4 |
| B | 11,000 | f | f | 2 | 5,800 | f | f | 4 |
| J | f | — | — | — | — | — | — | — |
| C | 24,000 | >1 | P | 5 | 9,700 | >1 | P | 5 |
| H | 3,400 | >1 | P | 0 | f | — | — | — |
| K | 18,000 | >1 | P | 4 | f | — | — | — |
| D | 8,000 | >1 | P | 5 | 12,000 | f | f | 5 |
| E | 10,000 | >1 | P | 0 | f | — | — | — |
| F | 19,000 | >1 | P | 2 | f | — | — | — |
| | | | | | Comparative | | | |
| SPE | 54,000 | >1 | P | 5 | f | — | — | — |

In Table 6, P means that the Emulsion Formulation passed without separation of any type. f means that it failed and indicates the formation of a water layer which is indicative of coalescence of the internal phase.

The silicone polyethers and the emulsions containing the silicone polyethers according to this invention are of general utility and application. However, they are particularly useful in, and for preparing numerous types of over-the-counter personal care products for hair, skin, and the underarm. Thus, they are especially useful and can be used in hair conditioners, hair shampoos, skin care lotions, facial cosmetics, deodorants, and antiperspirants. In addition, they can be used in other types of personal care products such as skin creams, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising an emulsion containing a liquid $C_{12}$ to $C_{15}$ alkyl benzoate, and a silicone polyether having the formula

$$R_3SiO(R_2SiO)_x(RQSiO)_y(RQ'SiO)_zSiR_3$$

in which R is an alkyl group containing 1–6 carbon atoms; Q represents a polyoxyalkylene block containing a linking group and a terminating group, the polyoxyalkylene block being represented by —$R^b$—O—$(C_2H_4O)_p$—$(C_3H_6O)_s$—$R^c$, in which the linking group $R^b$ is —$C_mH_{2m}$—, the terminating group $R^c$ is hydrogen or an alkyl group of one to six carbon atoms, m in the linking group has a value of two to eight, p and s in the oxyalkylene segment of the block each have a value such that the oxyalkylene segment —$(C_2H_4O)_p$—$(C_3H_6O)_s$— of the polyoxyalkylene block has a molecular weight in the range of about 300 to about 5,000;

Q' represents an arylalkyl radical selected from the group consisting of phenylmethyl, 1-phenylethyl, 2-phenylethyl, 2-phenylpropyl, 1-phenylbutyl, 4-phenylbutyl, and 2-phenylheptyl;

x has a value of 0–500; y has a value of 1–50: and z has a value of 1–50.

2. A composition according to claim 1 in which Q' is 2-phenylpropyl.

3. A composition according to claim 1 in which x is 1–400.

4. A composition according to claim 1 in which p is 1–28 and s is 0–28.

5. A composition according to claim 1 in which s is 1–28.

* * * * *